«12» United States Patent
Fischer

«10» Patent No.: US 7,687,244 B1
«45» Date of Patent: Mar. 30, 2010

«54» CHROMOGENIC COMPOSITION FOR DETECTING SPILLED BLOOD AND ASSOCIATED METHODS

«76» Inventor: John Fischer, P.O. Box 508, Gotha, FL (US) 34734

«*» Notice: Subject to any disclaimer, the term of this patent is extended or adjusted under 35 U.S.C. 154(b) by 735 days.

«21» Appl. No.: 11/280,088

«22» Filed: Nov. 16, 2005

Related U.S. Application Data

«60» Provisional application No. 60/628,793, filed on Nov. 17, 2004.

«51» Int. Cl.
*C12Q 1/28* (2006.01)
*G01N 21/64* (2006.01)

«52» U.S. Cl. .............. 435/28; 435/4; 436/63; 436/66; 436/74; 436/166; 436/172

«58» Field of Classification Search ............ None
See application file for complete search history.

«56» References Cited

U.S. PATENT DOCUMENTS

| | | | | |
|---|---|---|---|---|
| 5,563,071 A | * | 10/1996 | Augurt | 436/66 |
| 5,632,972 A | * | 5/1997 | Williams et al. | 424/49 |
| 5,653,970 A | * | 8/1997 | Vermeer | 424/70.24 |
| 5,885,789 A | * | 3/1999 | Kardos et al. | 435/28 |
| 6,692,967 B1 | * | 2/2004 | Di Benedetto et al. | 436/63 |
| 6,713,049 B1 | * | 3/2004 | White et al. | 424/57 |
| 2003/0022188 A1 | * | 1/2003 | Macina et al. | 435/6 |

OTHER PUBLICATIONS

Miller (2003) Blood Reagents—Their Use and Their Effect on DNA. Royal Canadian Mounted Police Forensic Identification Operations Support Services Bulletin. pp. 1-6.*

* cited by examiner

*Primary Examiner*—Lisa J Hobbs
«74» *Attorney, Agent, or Firm*—Allen, Dyer, Doppelt, Milbrath & Gilchrist, P.A.

«57» ABSTRACT

A chromogenic composition for detecting spilled blood includes a mixture of an acidified aqueous solution containing reduced FD&C Blue #1 and hydrogen peroxide. The chromogenic composition has a relatively long shelf life and will produce a bright blue visible color when contacting blood, thereby being useful for detecting spilled blood and blood trails from wounded game.

15 Claims, No Drawings

CHROMOGENIC COMPOSITION FOR DETECTING SPILLED BLOOD AND ASSOCIATED METHODS

RELATED APPLICATION

This application claims priority from provisional application Ser. No. 60/628,793, which was filed on Nov. 17, 2004, and which is incorporated herein by reference in its entirety.

FIELD OF THE INVENTION

The present invention relates to the field of detection of spilled blood and, more particularly, to a chromogenic composition which generates a visible color upon contacting blood.

BACKGROUND OF THE INVENTION

Hunting is a popular sport in many areas of the country. When hunting, however, the prey is not always instantly killed when shot and the hunter must track the wounded animal to either finish the task or to recover the kill. As it flees, the wounded animal typically leaves behind a trail of blood on the ground and vegetation. It is by following this trail of blood that the hunter generally tracks the wounded game.

Blood, however, is very difficult to see on the ground and/or on vegetation, particularly for the hunter who may be red-green colorblind, a condition known to affect approximately 5-8% of men and about 0.5% of women. Ninety-nine percent of colorblind people fall in the groups known as "red weak" or "green weak," which means that they have particular difficulty detecting red or reddish-brown blood stains deposited on brown woodland ground and/or on green vegetation.

SUMMARY OF THE INVENTION

With the foregoing in mind, the present invention advantageously provides a chromogenic composition that will generate a bright blue color when contacting spilled blood. The blue color is easily discernible even by colorblind individuals and may be detected even in low light situations or in the dark by the use of a common flashlight, which most hunters would routinely carry. Accordingly, the composition of the invention is useful in any light condition, whereas previously used chemiluminescent and fluorescent reagents for blood tracking are primarily useful in low light or at night but were not easily visible in daylight, and certainly not in bright sunlight.

It should be understood that while a preferred use of the present chromogenic composition is for tracking a wounded game animal, it is also equally useful in crime scene investigations for detecting spilled blood. Additionally, those skilled in the art should understand that the term "chromogenic" is used herein in its commonly accepted sense to refer to a substance capable of chemical conversion into a pigment, that is, a substance which chemically generates a color.

In the present invention a chromogenic composition is employed in what is commonly referred to as a catalytic test for blood. A chemically reduced or colorless dye is oxidized in a reaction catalyzed by hemoglobin and/or catalase found in blood, in the presence of an oxidizer such as hydrogen peroxide, to rapidly form the parent dye colored product. While not intending to be bound by any particular explanation of how the invention works, it is believed that an illustrative formula for this process is as follows, wherein "$Chrom_{red}$" is reduced chromogen which is colorless, Hg is hemoglobin and "$Chrom_{ox}$" is oxidized chromogen which is colored:

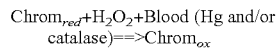

$$Chrom_{red} + H_2O_2 + Blood\ (Hg\ and/or\ catalase) \Longrightarrow Chrom_{ox}$$

In selecting an appropriate chromogen for use in the invention, several criteria were considered, as follows.
1. the chromogenic dye must pose substantially no health concerns for a user;
2. the chromogen must easily be reduced to, preferably, a colorless composition;
3. once in contact with blood the chromogen must produce a color easily seen and distinguishable from a variety of surfaces such as fall foliage, brown leaves, grass, vegetation and the ground;
4. the color generated must be visible by colorblind hunters, particularly those who are red-green colorblind, who have difficulty distinguishing the red brown color of blood from vegetation and other substrates.

Considering these criteria, food, drug and cosmetic dye Blue #1 (FD&C Blue #1) was chosen since it poses little or no health concerns as compared to other common blue dyes. It was also found that the blue color of oxidized FD&C Blue #1 was bright and easily distinguishable on a variety of naturally occurring substrates.

The skilled will recognize that the dye FD&C Blue #1 is also known by a variety of synonyms which may be found in standard chemical and pharmaceutical references. For example, the well known Merck Index and others. FD&C Blue #1 is also known as Cl Acid Blue 9, disodium salt; Brilliant Blue FCF, disodium salt; Ammonium, ethyl(4-(p-(ethyl(m-sufobenzyl)amino)-alpha-(o-sulfobenzylidene)-2,5-cyclo-hexadien-1-ylidine)(m-sulfobenzyl)-, hydroxide, inner salt, disodium (o-sulfophenyl)benzylidene)-2,5-cyclohexadien-1-ylidene) (m-sulfobenzyl)-, hydroxide, disodium; Benzenemethamaminium, N-ethyl-N-(4-((4-(ethyl(3-sulfophenyl)methyl)amine)phenyl)(2-sulfophenyl)-2,5-cyclohexadien-1-ylidine)-3-sulfo, hydroxide, inner salt, disodium salt; and D&C Blue #4. This list of synonyms should not, however, be considered definitive or exhaustive and is offered merely for purposes of illustration and to make this disclosure more complete. There may be other synonyms in use and which are intended to be covered in the claims appended hereto.

Additionally, since the FD&C Blue #1 dye is blue in color, this chromogenic dye may be used by color blind individuals to distinguish blood from backgrounds ranging in color from green to red brown.

DETAILED DESCRIPTION OF PREFERRED EMBODIMENTS

The present invention will now be described more fully hereinafter. Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below.

In addition, the materials, methods and examples given are illustrative in nature only and not intended to be limiting. Accordingly, this invention may be embodied in different forms and should not be construed as limited to the embodiments set forth herein. Rather, these embodiments are provided so that this disclosure will be thorough and complete and will fully convey the scope of the invention to those skilled in the art. Other features and advantages of the invention will be apparent from the following detailed description, and from the claims.

Hunters are frequently presented with the oft times difficult task of blood trailing their wounded or downed game animal that has fled from the area where it was initially shot. The task is made even more difficult in the Fall, when the fallen leaves on the ground and surrounding vegetation are predominantly red to red brown in color. Another complicating issue occurs when a visible blood trail suddenly stops, only to subsequently start again at some distance away. In the intervening distance, however, there are usually minute traces or blood spatters that are not visible to the unaided eye.

The present invention provides the hunter with an easily mixed and used reagent which will aid in following a blood trail. When the reagent comes in contact with blood, even minute traces of blood, it develops an intense brilliant blue color. The developed brilliant blue color easily distinguishes blood from the surrounding leaves and vegetation.

Another advantage of the present invention relates to the approximately 7% of males who are red-green colorblind. Many colorblind hunters do not perceive (or do so at a diminished capacity) the red to red brown color of blood. Blood that would be visible to most individuals is not detected by those who do not see the red to red brown color that the blood trail exhibits. However, most colorblind individuals can easily see a blue color. For this reason the invention is particularly well suited to aid in the search for blood. Many hunters who would be otherwise frustrated and would find it futile to track their game are now provided with a chance to find it. Moreover, blood trails that have been diluted by a heavy dew or light rain may also be detected and tracked with the present tracking reagent.

In the present composition it has been found that the reduced form of FD&C Blue #1 is easily prepared and that the final reduced chromogenic dye working solution is easily used in field application as a two part spray reagent.

Preparation of Reduced Dye Stock Solution.

The reduction of the chromogenic dye FD&C Blue #1 may be carried out in any suitable container, such as a boiling flask, or an Erlenmyer flask. In the present invention the dye was typically reduced in a 4 L ground glass fitted Erlenmyer flask.

In one preferred method of making a stock solution of FD&C Blue #1 in the reduced dye form, the following ingredients are mixed in a flask:

250 grams of mossy zinc;
40 grams of FD&C Blue #1 dye;
500 ml of a weak solution of lactic acid, which is made by combining 40 ml of 85% lactic acid diluted with 3353 mL of distilled water.

The above described mixture is then refluxed for approximately 2.5 to 3 hrs or until the solution changes from a blue to a mauve color. Once this has been carried out and the mauve color solution has been produced, the process is stopped.

Preparation of the Reduced Dye Stock Working Solution.

Five hundred (500) milliliters (ml) of the reduced dye stock solution is diluted with approximately 6750 ml of a 0.5% acid solution. The shelf life of this reagent is generally in excess of one year, depending on environmental conditions.

Use of the Composition.

A field working solution is prepared by combining approximately 400 ml of the reduced dye stock working solution with approximately 50 ml of a 3% solution of hydrogen peroxide.

This working solution is lightly mixed, then placed in a spray bottle, preferably an opaque plastic bottle which does not freely permit passage of light, as the composition is light-sensitive. The suspect blood area or blood trail is misted with the reagent. When the reagent comes in contact with blood a brilliant blue color develops.

Whereas a catalytic test for blood such as that based on a Luminol reagent is known to give numerous false positives, the present chromogenic composition results in fewer false positive reactions. These are typically triggered by substances naturally occurring in the environment.

Components of One Preferred Embodiment
I Stock Solution
250 g Mossy Zinc
40 g FD&C Blue #1
500 ml Lactic Acid Solution (40 mL lactic acid diluted with 3536 ml distilled water)
II Stock Working Solution (Reduced Dye)
500 ml reduced dye stock solution (above) diluted with 6750 mL of a 0.5% citric acid solution.
III Oxidizer
3% hydrogen peroxide Another Preferred Embodiment of the Present Composition A more expedient and cost effective method of producing reduced FD&C Blue #1 has also been developed. In place of mossy zinc, zinc powder is used in conjunction with distilled water allowing for much quicker reduction of the dye. Alternatively, the zinc powder and FD&C Blue #1 are diluted in the lactic acid solution. The mixture is then heated so as to reduce the dye, as described. The reduced dye solution is then diluted with a 0.5% citric acid solution, or alternatively with a 40% calcium chloride solution, which also acts as an antifreeze ingredient. The hydrogen peroxide is mixed with this solution prior to use of the composition.

It has been found that when the field working solution was stored in the field, freezing of the solution might become an issue. To this end calcium chloride was considered in order to lower the freezing point of the solution. Typically a 40% solution of calcium chloride lowers the freezing point to around 40° C. A 40% solution of calcium chloride, thus, lowered the freezing point of the composition, while reducing the amount of 0.5% citric acid required to acidify the solution. A lower level of calcium chloride may also be effective in keeping the working solution from freezing, for example, a solution of from approximately 25 to 40% calcium chloride may be employed. Other antifreeze reagents, including alcohols such as glycols, glycol ether, and ethanol are useful in the invention. Ethylene glycol, however, while it works in the invention and is intended to be covered by the appended claims, is not preferred for use due to its relatively sweet taste and toxicity to animals. However, propylene glycol, hexalene glycol and glycol DB may be employed as preferred ingredients in the inventive composition.

Forty percent by volume of ethanol has been found to be an excellent antifreeze in the present composition. For example, a 60:40 mix of the dye stock working solution and ethanol will result in more than adequate protection from freezing for the chromogenic composition. Specially denatured ethanols (SD ethanols) are also effective antifreeze reagents for use in the invention.

Long term storage of the reduced FD&C Blue #1 working stock solution was found to occasionally result in development of an amorphous, gelatinous mass in the solution. These gelled solutions also exhibited a pale green coloration, indicating that some oxidation of the chromogenic dye had occurred, lowering the overall efficiency of the solution. This concern is eliminated by the inclusion in the composition of an appropriate preservative, such as sodium ascorbate. It should be noted that the use of sodium ascorbate, though somewhat diminishing the reactivity of the solution, did not interfere with color formation. Therefore; sodium ascorbate remains one preferred preservative for use herein.

A reduced dye stock working solution containing 0.1% sodium sulfite produced better results, although some diminished reactivity was noted in a long term test. Nevertheless, this preservative showed better performance than the reagent including 0.05% sodium ascorbate. Other preservatives may be useful in the invention as well, for example, erythorbic acid, however; 0.1% sodium sulfite content is a preferred preservative.

In yet another embodiment of the invention, use of a 0.5% solution of potassium bitartrate as replacement for the 0.5% citric acid solution in acidifying the stock working reduced dye solution was found to increase the reactivity and color development. This may be a preferred reagent for acidifying the stock working reduced dye solution.

Additional Preferred Composition

Yet another preferred embodiment of the presently described chromogenic composition is made as follows.

Add 200 g powder zinc and 40 g FD&C Blue #1 dye to a 4000 mL Erlenmyer flask. Add 500 ml distilled water to the flask and reflux for 1.5 hrs. or until solution turns a mauve to brown color. Decant the solution and filter to remove residual zinc powder from the reduced dye solution.

Add 500 ml of reduced dye solution to 2500 ml of a 25-40% calcium chloride solution. To this solution add 250 ml of a 0.5% citric acid solution.

Add to the above solution 3.25 g sodium sulfite as a preservative. The stock working reduced dye solution is then complete.

Oxidizer Modification

One preferred method of reducing the freezing point of the 3% hydrogen peroxide is to add from 25 to 40 g of calcium chloride to each 100 mL of hydrogen peroxide.

In summary, this preferred embodiment of the present chromogenic composition is as follows.

I Stock Solution
  200 g powdered zinc
  40 g FD&C Blue #1
  500 ml distilled water
II Stock Working Solution (Reduced Dye)
  500 ml of new reduced dye stock solution (above) diluted with 2500 ml of a 25-40% calcium chloride solution. Add 250 ml of a 0.5% citric acid solution. Add 3.25 g sodium sulfite preservative.
III Oxidizer
  Prepare the 25 to 40% calcium chloride solution in 3% hydrogen peroxide.

Packaging Considerations

The skilled will realize that, for example, hydrogen peroxide is known to be light-sensitive and to degrade in the presence of light. The chromogenic dye solution may also be affected by light and should be preferably protected from exposure to light. Accordingly, the following may be packaged as a kit for use in the field.

Solution A
  50 ml of 3% hydrogen peroxide.
Solution B
  400 ml of reduced dye stock working solution.

As noted, both solutions are light-sensitive and are preferably stored in amber, opaque polyethylene bottles. For field use solution A is added to solution bottle B and gently mixed together. A pump sprayer head which may be included in the kit, is then placed on bottle B. For actual use in the field, an application of the field working solution is sprayed in a fine mist over the area suspected to contain blood.

Shelf Life

The A and B reagents of the present composition will remain stable and usable in an unmixed condition in excess of one year, even in the field. Temperatures above 90 to 100° F., however, may reduce the shelf life of the reagents. Once the reagents have been mixed (reduced dye+hydrogen peroxide) the usable life is generally 3 to 4 months, which is sufficient to cover most hunting seasons. Testing of the invention at ambient temperatures of between about 0 to 32° F. indicated that the reagents will react and produce color even in freezing conditions, however; as with any other chemical reaction, the reaction time and, hence, color development will be somewhat slower.

In the specification there have been disclosed typical preferred embodiments of the invention, and although specific terms may have been employed, the terms are used in a descriptive sense only and not for purposes of limitation. The invention has been described in considerable detail and it will be apparent that various modifications and changes can be made within the spirit and scope of the invention as described in the foregoing specification and as defined in the appended claims.

The invention claimed is:

1. A chromogenic composition for detecting spilled blood, said composition comprising:
  an acidified aqueous solution containing FD&C Blue #1 in a reduced state so as to render the solution colorless; and
  hydrogen peroxide.

2. The composition of claim 1, further comprising an effective preservative.

3. The composition of claim 1, further containing sodium sulfite in an effective amount as a preservative.

4. The composition of claim 1, further comprising an effective antifreeze.

5. The composition of claim 1, further comprising calcium chloride as an effective antifreeze.

6. The composition of claim 1, wherein said acidified aqueous solution contains at least one or more acids selected from citric acid, lactic acid, ascorbic acid, tartaric acid, their salts, and combinations thereof.

7. A chromogenic composition for detecting spilled blood, said composition comprising:
  an acidified aqueous solution containing FD&C Blue #1 in a reduced state so as to render the solution colorless;
  an effective antifreeze; and
  hydrogen peroxide.

8. The composition of claim 7, wherein said effective antifreeze comprises calcium chloride.

9. The composition of claim 7, wherein said effective antifreeze comprises calcium chloride in a concentration of from approximately 25-40%.

10. The composition of claim 7, wherein said effective antifreeze comprises an alcohol.

11. The composition of claim 7, wherein said effective antifreeze comprises a glycol.

12. The composition of claim 7, wherein said effective antifreeze comprises a glycol selected from propylene glycol, hexalene glycol, glycol DB, ethylene glycol and combinations thereof.

13. A chromogenic composition for detecting spilled blood, said composition comprising:
- an acidified aqueous solution containing FD&C Blue #1 in a reduced state so as to render the solution colorless;
- ethanol in an amount effective as an antifreeze; and
- hydrogen peroxide.

14. The composition of claim 13, wherein said effective antifreeze comprises denatured ethanol.

15. The composition of claim 13, wherein said effective antifreeze comprises approximately 40% by volume of an ethanol.

* * * * *